United States Patent [19]

Gillies

[11] Patent Number: 5,650,150
[45] Date of Patent: Jul. 22, 1997

[54] RECOMBINANT ANTIBODY CYTOKINE FUSION PROTEINS

[76] Inventor: Stephen D. Gillies, 245 Leavitt St., Hingham, Mass. 02043

[21] Appl. No.: 281,238

[22] Filed: Jul. 27, 1994

Related U.S. Application Data

[63] Continuation of Ser. No. 788,765, Nov. 7, 1991, abandoned, which is a continuation-in-part of Ser. No. 612,099, Nov. 9, 1990, abandoned.

[51] Int. Cl.$^6$ .................... A61K 39/395; A61K 39/40; A61K 45/05; C12P 21/04
[52] U.S. Cl. .................... 424/134.1; 424/133.1; 424/85.1; 435/69.7
[58] Field of Search .................... 530/387.1, 387.3, 530/388.3, 387.8; 424/134.1, 133.1, 159.1, 147.1, 155.1; 435/69.7

[56] References Cited

U.S. PATENT DOCUMENTS

| | | | |
|---|---|---|---|
| 4,196,265 | 4/1980 | Koprowski et al. | 435/2 |
| 4,469,797 | 9/1984 | Albarella | 436/536 |
| 4,676,980 | 6/1987 | Segal et al. | 424/85 |
| 4,946,778 | 8/1990 | Ladner et al. | 435/69.6 |
| 5,073,627 | 12/1991 | Curtis et al. | 530/351 |
| 5,114,711 | 5/1992 | Bell et al. | 424/85.1 |
| 5,314,995 | 5/1994 | Fell et al. | 530/351 |

FOREIGN PATENT DOCUMENTS

| | | |
|---|---|---|
| 0294703 | 12/1988 | European Pat. Off. . |
| 0308936 | 3/1989 | European Pat. Off. . |
| 0314317 | 5/1989 | European Pat. Off. . |
| 0 375 562 | 6/1990 | European Pat. Off. . |
| 0 396 387 | 11/1990 | European Pat. Off. . |
| 0439095 | 7/1991 | European Pat. Off. . |
| 8601533 | 3/1986 | WIPO . |
| 8800052 | 1/1988 | WIPO . |
| 8809344 | 12/1988 | WIPO . |
| 8902922 | 4/1989 | WIPO . |
| WO 90/03801 | 4/1990 | WIPO . |
| WO91/13166 | 9/1991 | WIPO . |
| WO91/14438 | 10/1991 | WIPO . |

OTHER PUBLICATIONS

Neerberger et al. "Nature" vol. 312 p. 604 1984.
Harris et al. Trends Biotechnol. vol. 11 p. 42, 1993.
Karpovsky et al. (1984) J. Experimental Medicine 160:1686–1701.
Kranz et al. (1984) Proc. Natl. Acad. Sci. USA 81:7922–7926.
Henkart (1985) Ann. Rev. Immunol 3:31–58.
Liu et al. (1985) Proc. Natl. Acad. Sci. USA 82:8648–8652.
Jung et al. (1986) Proc. Natl. Acad. Sci. USA 83:4479–4483.
Murphy et al. (1986) Proc. Natl. Acad. Sci. USA 83:8258–8262.
Perez et al. (1986) J. Experimental Medicine 163:166–178.
Santon et al. (1986) Cancer Research 46:4701–4705.
Shen et al. (1986) J. Immunology 137:3378–3382, No. 11.
Williams et al. (1987) Protein Engineering 1:493–498, No. 6.
Bacha et al. (1988) J. Experimental Medicine 167:612–622.
Chaudhary et al. (1988) Nature 335:369–372.
Liu et al. (1988) Science 239:395–398.
Till et al. (1988) Science 242:1166–1168.
Capon et al. (1989) Nature 337:525–530.
Pastan et al. (1989) J. Bio.Chem. 264:15157–15160, No. 26.
Gillies et al. (1989) J. Immuno. Methods 125:191–202.
Gillies et al. (1989) Bio/Technology 7:799–804.
Shin et al. (1990) Proc. Natl. Acad. Sci. USA 87:5322–5326.
Taniguchi et al. (1983) Macmillan Journals Ltd. "Structure and expression of a cloned cDNA for human interleukin–2".
Gasson et al. (1984) Science 226:1339–1342.
Nedwin et al. (1985) Nucleic Acids Res. 13:6361–6373.
Goeddel et al. (1986) "Tumor Necrosis Factors: Gene Structure and Biological Activities" pp. 597–609.
Beutler et al. (1988) Ann. Rev. Biochem. 57:505–518.
Paul et al. (1988) Ann. Rev. Immunol. 6:407–438.
Gillies et al. (1990) Hum. Antibod. Hybridomas 1:47–54.
Williams et al. (Abstract).
Biosis Abstract No. 91:367080, Biol. Abstr. 92:55305 and *Biochim.* and *Biophys.* Acta 1096:345–354 (1991).
Herrmann et al. (1989) *J. Clin. Oncol.* 7(2):159–167; "Hematopoeitic Responses With Advanced Malignancy Treated With Recombinant Human Granulocyte–Macrophage Colony–Stimulating Factor".

*Primary Examiner*—Lila Feisee
*Assistant Examiner*—Ray F. Ebert
*Attorney, Agent, or Firm*—Testa, Hurwitz & Thibeault, LLP

[57] ABSTRACT

Immunoconjugates for the selective delivery of a cytokine to a target cell are disclosed. The fusion proteins are comprised of an immunoglobulin heavy chain having a specificity for the target cell, such as a cancer or virus-infected cell, and a cytokine, such as lymphotoxin, tumor necrosis factor alpha, interleukin-2, or granulocyte-macrophage colony stimulating factor, joined via its amino terminal amino acid to the carboxy-terminus of the immunoglobulin. Nucleic acid sequences encoding these fusion proteins and methods of their preparation by genetic engineering techniques are also disclosed.

21 Claims, 9 Drawing Sheets

RECOMBINANT ANTIBODY CYTOKINE FUSION PROTEINS

This is a continuation of application Ser. No. 07/788,765 filed Nov. 7, 1991 (now abandoned), which is a continuation-in-part of application Ser. No. 07/612,099, filed Nov. 9, 1990 (now abandoned), the disclosures of which are incorporated herein by reference.

BACKGROUND OF THE INVENTION

The present invention relates generally to therapies involving the selective destruction of cells in vivo and to compositions of matter useful in the treatment of various cancers and vital infections. In particular, this invention relates to genetically engineered antibody fusion constructs capable of targeting an infected cell, and eliciting a localized inflammatory response such that the cell is killed or neutralized.

Tumor necrosis factor (TNF$\alpha$) and lymphotoxin (LT or TNF$\beta$) were first identified on the basis of their ability to directly kill certain tumors. However, many other biological activities are now attributed to these closely related cytokines. These include effects on a variety of cell types, such as the induction of histocompatibility antigens and adhesion receptors, as well as those resulting in inflammation, vascular permeability changes and mononuclear cell infiltration (Goeddel, D. V. et al. (1986) Symp. Quant. Biol. 51:597, Cold Spring Harbor; Beutler, B. and Cerami, A. (1988) Ann. Rev. Biochem. 57:505; Paul N. L. and Ruddle, N. H. (1988) Ann. Rev. Immunol. 6:407). The very short half-life of both TNF$\alpha$ and LT ensures that these inflammatory reactions do not occur systematically, but only at the sites of release from TNF-producing cells.

This ability to elicit a localized inflammatory response could be used in the treatment of solid tumors or other diseased tissue. For example, if it were possible to specifically deliver either TNF$\alpha$ or LT to a tumor site, a local inflammatory response could lead to an influx of effector cells such as natural killer cells, large granular lymphocytes, and eosinophils, i.e., the cells that are needed for antibody-dependent cellular cytotoxicity (ADCC) activity.

A way to deliver the lymphokine to a specific site in vivo is to conjugate it to an immunoglobulin specific for the site. However, the fusion of protein domains to the carboxy-termini of immunoglobulin chains or fragments can have unexpected consequences for the activities of both the protein to be fused and the immunoglobulin, particularly as far as antigen binding, assembly and effector functions are concerned. For example, the desired biological functions of the individual proteins may not be maintained in the final product.

Another potential problem with expressing proteins, such as the lymphokine LT, as a fusion protein to an immunoglobulin chain is that the native molecule exists in solution as a trimer and binds more efficiently to its receptor in this form. Thus, it seems unlikely that trimerization could still occur when LT is attached to an immunoglobulin heavy (H) chain via amino terminus and is assembled into an intact Ig molecule containing two paired H chain fusion polypeptides. Secondly, the ability of the fused LT to bind its receptor may be severely compromised if a free amino terminus is required for receptor binding activity. In fact, it has been postulated that the amino and carboxy-termini of TNF$\alpha$, and, by analogy, LT, together form a structure that is required for receptor interaction.

It is an object of the invention to provide compositions of matter capable of selectively destroying cells in vivo, and therapeutic methods for accomplishing this. It is also an object of the invention to provide compositions of matter and therapeutic methods for selectively delivering a cytokine to a target cell for the purpose of destroying the target cell either directly or by creating an environment lethal to the target cell.

SUMMARY OF THE INVENTION

This invention relates to immunoconjugates which include an immunoglobulin (Ig), typically a heavy chain, and a cytokine, and to the use of the immunoconjugates to treat disease. The immunoconjugates retain the antigen-binding activity of the Ig and the biological activity of the cytokine and can be used to specifically deliver the cytokine to the target cell.

The term "cytokine" is used herein to describe proteins, analogs thereof, and fragments thereof which are produced and excreted by a cell, and which elicit a specific response in a cell which has a receptor for that cytokine. Preferable cytokines include the interleukins such as interleukin-2 (IL-2), hematopoietic factors such as granulocyte-macrophage colony stimulating factor (GM-CSF), and tumor necrosis factor alpha (TNF$\alpha$).

The term "lymphokine" as used herein describes proteins, analogs thereof, and fragments thereon produced by activated lymphocytes, and having the ability to elicit a specific response in a cell which has a receptor for that lymphokine, e.g., lymphotoxins. Lymphokines are a particular type of cytokine.

In preferred embodiments, the immunoconjugate comprises a chimeric Ig chain having a variable region specific for a target antigen and a constant region linked through a peptide bond at the carboxy terminus of the heavy chain to the cytokine.

Immunoconjugates of the invention may be considered chimeric by virtue of two aspects of their structure. First, the immunoconjugate is chimeric in that it includes an immunoglobulin chain (typically but not exclusively a heavy chain) of appropriate antigen binding specificity fused to a given cytokine. Second, an immunoconjugate of the invention may be chimeric in the sense that it includes a variable region and a constant region which may be the constant region normally associated with the variable region, or a different one and thus a V/C chimera; e.g., variable and constant regions from different naturally occurring antibody molecules or from different species. Also embraced within the term "immunoconjugate" are constructs having a binding domain comprising framework regions and variable regions (i.e., complementarity determining regions) from different species, such as are disclosed by Greg Winter et al., GB2, 188, 638. Preferably, the cytokine of the immunoconjugate can be a protein which naturally forms a dimeric or multimeric structure when unfused, such as LT or TNF$\alpha$.

In a preferred embodiment, the chimeric Ig chain comprises a heavy (H) chain which includes the CH1, CH2 and CH3 domains. A proteolytic cleavage site may be located between the Ig heavy chain and the cytokine so that, when the conjugate reaches the target cell, the cytokine is cleaved from the heavy chain. A "proteolytic cleavage site" is an amino acid sequence recognizable by a protease with cleaves either within or proximal to the sequence. Preferably, the variable region is derived from a mouse (i.e. its DNA sequence or its amino acid sequence is based on a DNA or amino acid sequence of mouse origin) and the constant region (preferably including the framework region amino acids of the variable region) is derived from a human;

and the variable region of the heavy chain is derived from an Ig specific for a virus-infected cell, or for a tumor-associated or viral antigen. Preferably, the chimeric Ig chain can be assembled into the immunoconjugate by combining it with an appropriate counterpart (light or heavy) chain to form a monovalent antigen-binding region, which can then be associated to produce a divalent immunoconjugate specific for the target antigen.

The invention also features DNA constructs encoding the above-described immunoconjugates, and cell lines, e.g., myelomas, transfected with these constructs.

The invention also includes a method of selectively delivering a cytokine to a target cell, which method includes providing a cytokine immunoconjugate including a chimeric Ig chain including an Ig heavy chain having a variable region specific for the target cell and a constant region joined at its carboxy terminus by a peptide bond to a cytokine, and an Ig light chain combined with the chimeric Ig heavy chain, forming a functional antigen-binding site, and administering the immunoconjugate in an amount sufficient to reach the target cell to a subject harboring the target cell.

The invention thus provides an immunoconjugate in which the antigen binding specificity and activity of an antibody are combined in one molecule with the potent biological activity of a cytokine. An immunoconjugate of the invention can be used to deliver selectively a cytokine to a target cell in vivo so that the cytokine can exert a localized biological effect, such as a local inflammatory response, stimulation of T cell growth and activation, and ADCC activity. Such conjugates, depending on their specificity and biological activity can be used to treat diseases involving viral infections, or cancer, by targeted cell lysis, according to methods of the invention.

DESCRIPTION OF THE DRAWINGS

The foregoing and other objects of the present invention, and the various features thereof, may be more fully understood from the following description, when read together with the accompanying drawings, in which:

FIGS. 2A–D are diagrams of the construction of fusion proteins between LT and the human Ig H chain; wherein

FIGS. 4A–B are graphs showing the comparison of LT cytolytic activities for native LT (Δ--Δ), CH2-LT (o--o) or CH3-LT (o--o, filled in) immunoconjugates. A sensitive clone of the mouse fibroblast line 929 was used in the 1-day assay with mitomycin C. Relative cell survival was quantitated by staining with crystal violet and measuring the absorbance at 630 nm.

FIG. 5 is a graph of the effect of pH during purification on the cytostatic activity of CH3-LT. The activities of native LT (o--o), CH3-LT in culture supernatant (Δ--Δ), CH3-LT purified by protein A Sepharose chromatography (¤--¤) and CH3-LT purified at pH 6.5 (Δ--Δ) were compared in the cytostatic assay (in the absence of mitomycin C) using a mouse 929 subclone;

DETAILED DESCRIPTION OF THE INVENTION

The invention relates to immunoconjugates useful for killing a malignant or virus-infected target cell. The immunoconjugate includes a conjugate of an antibody portion having a specificity for a surface antigen on a virus-infected or malignant cell, and a cytokine.

Figure 1:
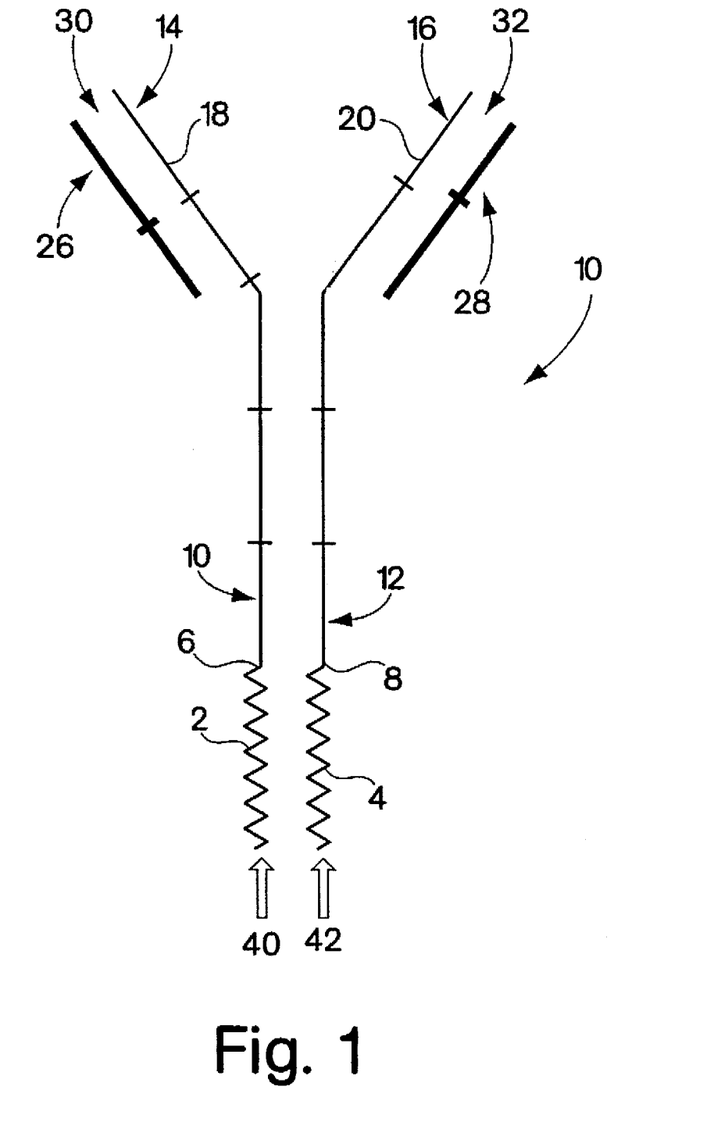
FIG. 1 is a schematic representation of one embodiment of the immunoconjugate of the present invention.
Figure 2A:
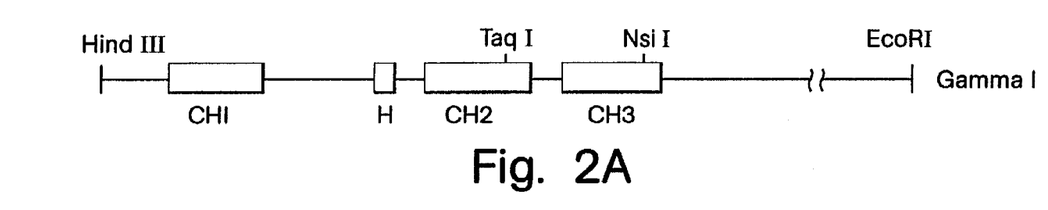
FIG. 2A is a map of a human Cγ1 gene fragment cloned in plasmid pBR322.
Figure 2B:
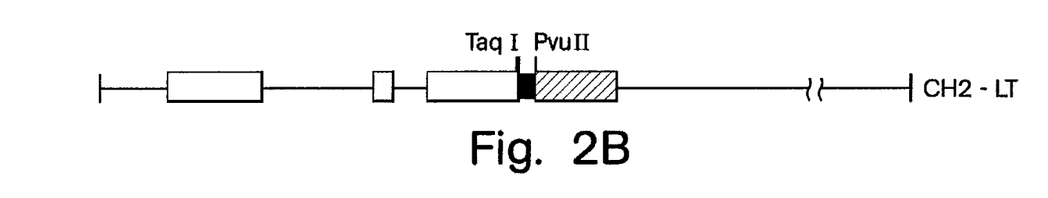
FIG. 2B shows the Cγ1 gene fused to LT at the end of the CH2 domain.
Figure 2C:
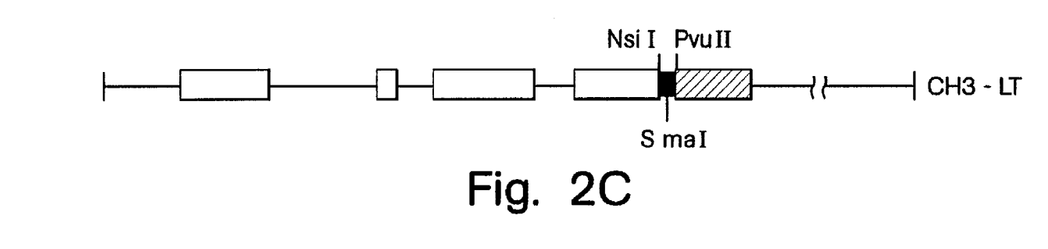
FIG. 2C shows the Cγ1 gene fused to LT at the end of the CH3 domain.
Figure 2D:
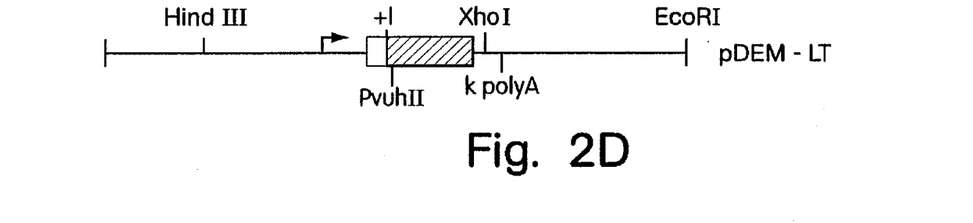
FIG. 2D shows the cDNA encoding LT cloned in expression vector pDEM including promoter (arrow), the natural leader peptide of LT (open box), the first residue of the mature protein (+1) and mouse κ L-chain poly A and 3'untranslated sequence. Open boxes represent protein coding regions of Cγ1 in A–C; black boxes represent synthetic linkers used to join the protein coding sequences; and striped boxes represent LT coding sequences.

FIG. 1 shows a schematic view of a representative immunoconjugate 10. In this embodiment, cytokine molecules 2 and 4 are peptide bonded to the carboxy termini 6 and 8 of CH3 regions 10 and 12 of antibody heavy chains 14 and 16. $V_L$ regions 26 and 28 are shown paired with $V_H$ regions 18 and 20 in a typical IgG configuration, thereby providing two antigen binding sites 30 and 32 at the amino ends of immunoconjugate 10 and two cytokine receptor-binding sites 40 and 42 at the carboxy ends of immunoconjugate 10. Of course, in their broader aspects, the immunoconjugates need not be paired as illustrated.

The immunoconjugates of this invention can be produced by genetic engineering techniques; i.e., by forming a nucleic acid construct encoding the chimeric immunoconjugate. Preferably, the gene construct encoding the immunoconjugate of the invention includes, in 5' to 3' orientation, a DNA segment which encodes a heavy chain variable region, a DNA segment encoding the heavy chain constant region, and DNA coding for the cytokine. The fused gene is assembled in or inserted into an expression vector for transfection of the appropriate recipient cells where it is expressed. The hybrid chain can be combined with a light (or heavy) chain counterpart to form monovalent and divalent immunoconjugates.

The cytokine can be any cytokine or analog or fragment thereof which has a therapeutically valuable biological function. Useful cytokines include the interleukins and hematopoietic factors such as interleukin-2 (IL-2) and granulocyte-macrophage colony stimulating factor (GMCSF). Lymphokines such as LT and TNF∝, which require the formation of multimeric structures to function, can also be used. The gene encoding the lymphokine or cytokine can be cloned de novo, obtained from an available source, or synthesized by standard DNA synthesis from a known nucleotide sequence. For example, the DNA sequence of LT is known (see, e.g. Nedwin et al. (1985) Nucleic Acids Res. 13:6361), as are the sequences for interleukin-2 (see, e.g., Taniguchi et al. (1983) Nature 302:305–318), granulocyte-macrophage colony stimulating factor (see, e.g., Gasson et al. (1984) Science 266:1339–1342), and tumor necrosis factor alpha (see, e.g., Nedwin et al. 1. Ibid.)

The heavy chain constant region for the conjugates can be selected from any of the five isotypes: alpha, delta, epsilon, gamma or mu. Heavy chains or various subclasses (such as the IgG subclasses 1–4) can be used. The light chains can have either a kappa or lambda constant chain. DNA sequences for these immunoglobulin regions are well known in the art. (See, e.g., Gillies et al. (1989) J. Immunol. Meth. 125:191).

In preferred embodiments, the variable region is derived from an antibody specific for the target antigen (an antigen associated with a diseased cell such as a cancer cell or virus-infected cell), and the constant region includes the CH1, CH2 and CH3 domains. The gene encoding the cytokine is joined, (e.g., by appropriate linkers, e.g., by DNA encoding $(Gly_4-Ser)_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the cytokine, can be designed to provide for proteolytic release of the cytokine at the target site. For example, it is well known that plasmin and trypsin cleave after lysine and arginine residues at sites that are accessible to the proteases. Many other site-specific endoproteases and the amino acid sequences they attack are well-known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

The target antigen can be a cell surface antigen of a tumor cell, a virus-infected cell or another diseased cell. Genes encoding appropriate variable regions can be obtained generally from Ig-producing lymphoid cells. For example, hybridoma cell lines producing Ig specific for tumor associated antigens or viral antigens can be produced by standard somatic cell hybridization techniques. (See, e.g., U.S. Pat. No. 4,96,265.) These Ig-producing cell lines provide the source of variable region genes in functionally rearranged form. The variable region genes will typically be of murine origin because this murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate protein. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion. (see, Gillies et al. (1989) Biotechnol. 7:798–804). Alternative methods include electroporation or calcium phosphate precipitation.

Other useful methods of producing the immunoconjugates include the preparation of an RNA sequence encoding the construct and its translation in an appropriate in vivo or in vitro system.

The immunoconjugate of this invention can be used to deliver selectively a cytokine to a target cell in vivo so that the cytokine can exert a localized biological effect such as a local inflammatory response, stimulation of T cell growth and activation, and ADCC activity. A therapeutically effective amount of the immunoconjugate is administered into the circulatory system of a subject harboring the target cell.

The invention is illustrated further by the following non-limiting Examples.

1. Plasmid Construction

Described below is the construction of PdHL2, a plasmid which contains the human Cγ1 heavy and kappa light chain gene sequences as well as insertion sites for V region cDNA cassettes (Gillies et al. (1989) J. Immunol. Meth. 125:191). This plasmid may be used as a starter plasmid for constructing any IgH chain cytokine fusion. For example, PdHL2 was used for the expression of Ig/LT fusion proteins. A LT cDNA was isolated from a human peripheral blood leukocyte library cloned in λgt10. The sequence was identical to that reported in the literature by Nedwin et al. (Nucleic Acids Res (1985) 13:6361). The cDNA was inserted into vector pDEM (Gillies et al., ibid) as an XhoI fragment after first removing most of the 3' untranslated region with Bal31 nuclease. The resulting plasmid, pDEM-LT (FIG. 2), expresses (in transfected cells) a fusion mRNA with a 5' untranslated sequence derived from the metallothionein (MT) promoter, the LT coding sequence and a 3' untranslated sequence and a poly A addition signal from the mouse Cκ gene. Fusion protein-encoding vectors were constructed by ligating HindIII to TaqI (CH2-LT) or HindIII to NsiI (CH3-LT) fragments of the human Cγ1 gene to HindIII and PvuII digested PDEM-LT using synthetic DNA linkers (FIG. 2). These linkers:

(5'-CGAAGAAACCATCTCCAAA/CTCCCTGGTGTTGGCCTCAC ACCTTCAG-3' (for CH2-LT); and

5'-TGAGGCTCTGCACAACCACTACACGCAGAAGAGCCTCTCCCT GTCCCCGGGTAAA/CTCCCTGGTGTTGGCCTCACACCTTCAG-3')

provide the protein coding sequence from the unique site (NsiI or TaqI) to the end of the heavy-chain domain (indicated by the slash), and join them to the amino terminus of the mature form of LT (up to the unique PvuII site). The linker for the CH3 fusion protein also includes a silent mutation that creates a SmaI site close to the end of the domain for future use in constructing fusion proteins. The DNA sequences at the junction of each construct were confirmed and each HindIII to EcoRI fragment was inserted into plasmid pdHL2-VCγ1κ(14.18). This plasmid contains the V cassettes for the ch14.18 anti-ganglioside GD2 antibody (Gillies et al., ibid.).

2. Cell Culture and Transfection

Sp2/0 Ag14 mouse hybridoma cells were maintained and transfected as described by Gillies et al. (BioTechnology (1989) 7:8799). Drug selection in methotrexate (MTX) was initiated 24 hours after transfection by adding an equal volume of medium containing MTX at 0.1 µM. Two additional feedings with selection medium were done at 3 day intervals. Transfectants secreting human Ig determinants were identified by ELISA (Gillies et al., 1989. ibid), grown in medium containing increasing concentrations of MTX, and subcloned by limiting dilution in medium containing MTX at 5 µM.

3. Purification and Characterization of Fusion Proteins

Proteins were biosynthetically labeled by incubating transfected cells ($1\times10^6$/mL) for 16 hr in growth medium containing $^{35}$S-methionine (50 µCi/mL-Amersham). Culture supernatants were then clarified by centrifugation in a microcentrifuge and the labeled proteins were immmunoprecipitated with polyclonal anti-human κ chain antisera (Jackson Immunoresearch, Bar Harbor, Me.) and protein A Sepharose (Repligen, Corp., Cambridge, Mass.). Protein samples were boiled for 5 min. in gel sample buffer in the presence or absence of 2-mercaptoethanol and analyzed on a 7% polyacrylamide gel. Proteins were detected by fluorography (diphenyloxazole in DMSO) and autoradiography.

Unlabeled proteins were purified from spent suspension culture medium by either immunoaffinity chromatography with a monoclonal anti-human κ antibody for the CH2-LT protein or by protein A Sepharose chromatography for the CH3-LT protein. All materials were concentrated by membrane dialysis into PBS. An alternative procedure for purification of the CH3-LT protein was developed to prevent the loss of LT activity during elution from the protein A column. Spent culture media was diluted with three volumes of 10 mM sodium phosphate buffer (pH 6.5) and loaded onto a Bakerbond AbX (J. T. Baker) column at room temperature. The column was washed with 10 mM sodium phosphate buffer until the absorbance returned to baseline and then with PBS, pH 6.5 (150 mM NaCl, 10 mM sodium phosphate, pH 6.5). The CH3-LT protein was eluted with 150 mM NaCl, 50 mM sodium phosphate, pH 6.5.

4. Activity Assay

The antigen binding activity of the Ig-LT proteins was measured as described in Gillies et al. (J. Immunol. Meth. (1989) 125:191), and LT activity was determined in the cytolytic or cytostatic assay (Kahn et al. (1982)) utilizing the 159124T2.5 subclone of the mouse L929 cell line (provided by Dr. H. Schreiber, University of Chicago). Cells were seeded into 96-well plates at $4\times10^4$ cells per well, with (cytolytic) or without (cytostatic) mitomycin C (2 µg/mL), and 10 µL of the test sample was added after 24 hr. Cells were stained either 24 or 48 hr later (see FIG. descriptions) with crystal violet and the amounts of dye retained in the wells were compared to those of untreated wells and those receiving the LT standard (R&D Systems). The same assay was also carried out with the GD2-bearing human melanoma line M21, originally provided by D. L. Morton, University of California, Los Angeles. The latter cell line was also used for measuring CDC and ADCC activity as described earlier (Gillies et al. (1990) Human Antibody. Hybridomas 1:47)

5. Expression of Ig/LT Immunoconjugates

The Ig/LT immunoconjugates were made by directly fusing the cDNA sequence encoding the mature form of LT to the end of either the CH2 or CH3 exon of the human Cγ1 gene (FIG. 2) with the appropriate synthetic linkers. This gene fusion was then combined in a vector together with the V regions of murine antibody 14.18 and the human Cκ gene, and expressed in transfected Sp2/0 cells. These immunoconjugates were then expressed and tested for antigen binding activity and Ig chain assembly. The immunoconjugates retained antigen binding when measured in a competitive antigen binding ELISA (see below), and were assembled. Cells expressing these immunoconjugates were labeled with $^{35}$S-methionine, and the secreted proteins were analyzed by SDS-PAGE in the presence or absence of reducing agent.

Figure 3:
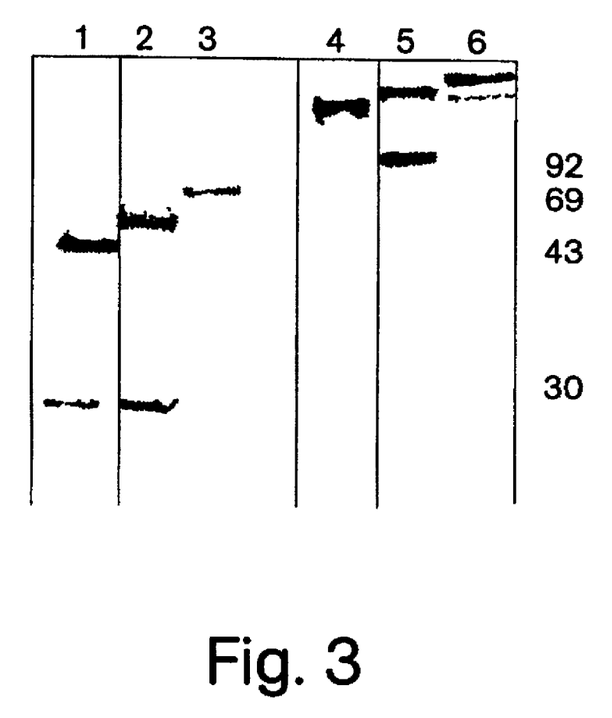
FIG. 3 is a strippled representation of an SDS-polyacrylamide gel showing an analysis of fusion protein chain assembly, wherein chimeric ch14.18 antibody is shown in lanes 1 and 4; CH2-LT is shown in lanes 2 and 5; and CH3-LT is shown in lanes 3 and 6. The position of stained marker proteins and their apparent molecular weights are indicated. The dried gel was exposed to film for either 4 hr (lanes 1 and 4) or 18 hr. Cells were labeled with $^{35}$S-methionine and secreted proteins were precipitated with an anti-human κ antiserum and protein A and analyzed on an SDS gel either reduced (lanes 1–3) or unreduced (lanes 4–6)

As seen in FIG. 3, the CH2-LT immunoconjugate was expressed as a mixture of whole (approximately 180 Kd) and half (90 Kd) molecules. The CH3-LT fusion protein, on the other hand, consisted entirely of fully assembled molecules. This result is not surprising since the CH3 domain is most responsible for Ig chain assembly. The reason why a portion of the CH2-LT did assemble, i.e. formed disulfide bonds in the hinge domain of the antibody, is likely due to the dimerization of the carboxy-terminal LT domains.

6. Biological Activity of Ig/LT Conjugates

Figure 4A:
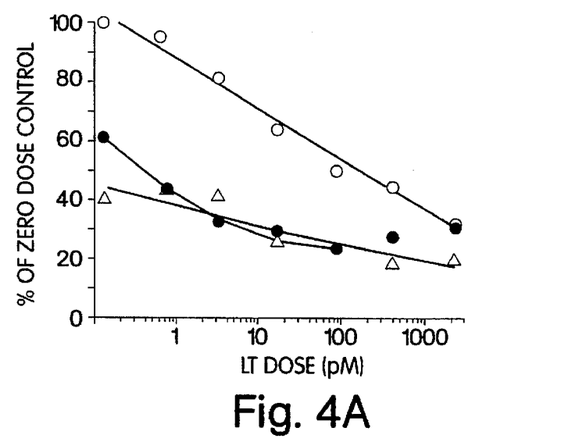
FIG. 4A shows culture supernatants from transfected cells assayed after first quantitating the conjugates by ELISA.

The LT activities of the CH2-LT and CH3-LT conjugates were compared in the standard cytolytic assay (Kahn, A. et al. (1982) "A standardized automated computer assisted micro-assay for lymphotoxin." In: *Human Lymphokines, Biological response modified*; (Kahn and Hill, eds.) Academic Press, New York, p. 23), using a mouse L929 subclone. This assay measures the ability of the immunoconjugate to bind to the TNF/LT receptor and trigger the active cell killing process in this cell line. When crude preparations (culture supernatants) were compared (FIG. 4A), CH3-LT was found to be much more active (nearly 100 fold by this assay) than CH2-LT and exhibited approximately the same specific activity per mole as the LT standard. This higher activity of CH3-LT is likely due to the increased proportion of fully assembled H-chain fusion proteins. Thus, the presence of the CH3 exon in the immunoconjugate may allow the H-chains to associate more efficiently, perhaps positioning the LT domains in a manner that allows for dimerization and, as a consequence, more LT receptor binding.

Figure 4B:
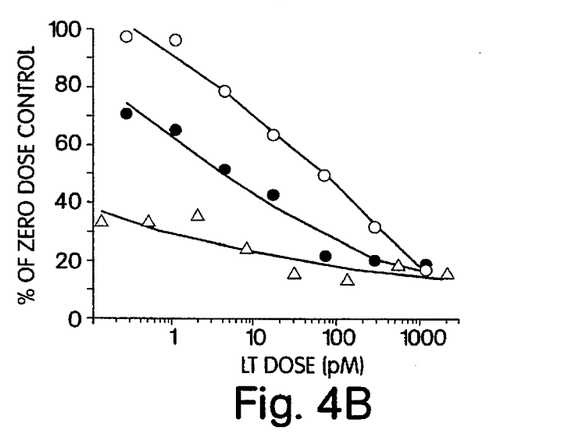
FIG. 4B shows purified proteins assayed following protein A Sepharose or immunoaffinity chromatography.

When purified preparations were compared, the difference in activities between CH2-LT and CH3-LT was still evident, but the activity of the conjugates, especially CH3-LT, was greatly reduced compared to the LT control (FIG. 4B). Since both proteins had been purified by using elution steps at acidic pH (i.e., less than pH4), the pH sensitivity of the culture supernatants was examined, and the LT activity was found to be very acid labile.

Figure 5:
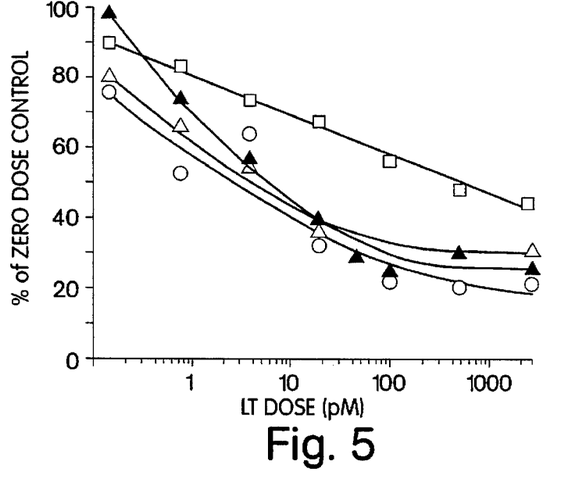
Figure 6A:
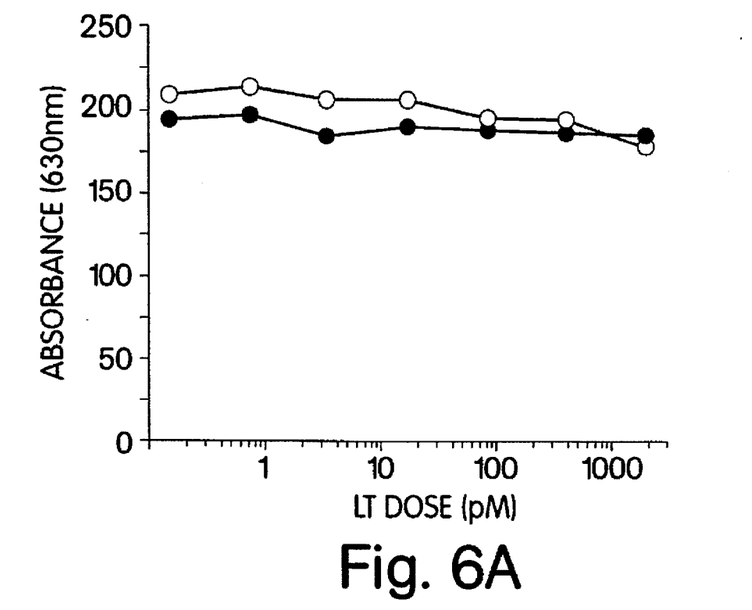
FIGS. 6A–B are graphs of the cytolytic and cytostatic activities of LT and CH3-LT GD2-positive M21 human melanoma cells. M21 cells were seeded in 96-well plates in the [Bpresence (FIG. 6A) or absence (FIG. 6B) of mitomycin C and dilutions of LT (o--o) or CH3-LT (o--o, filled in) were added. Relative cell growth was measured by staining wells with crystal violet after 48 hr and measuring the absorbance at 630 nm.
Figure 6B:
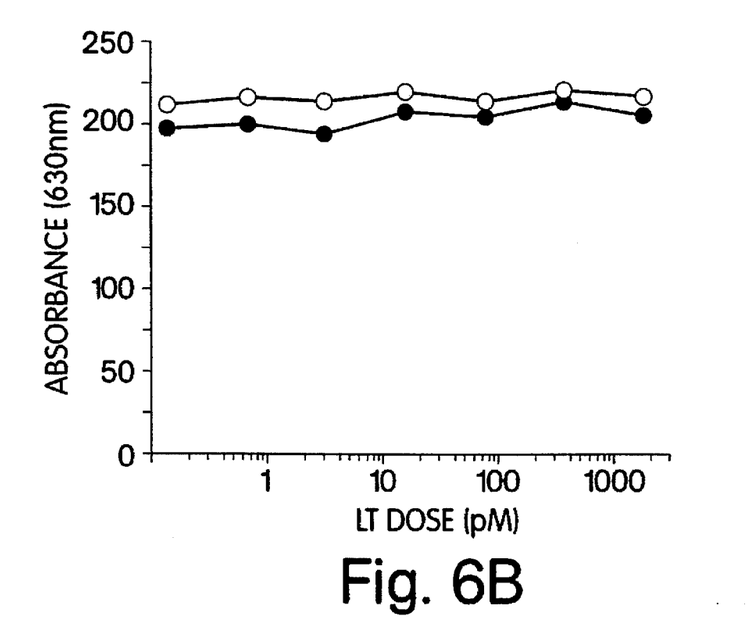
Figure 7:
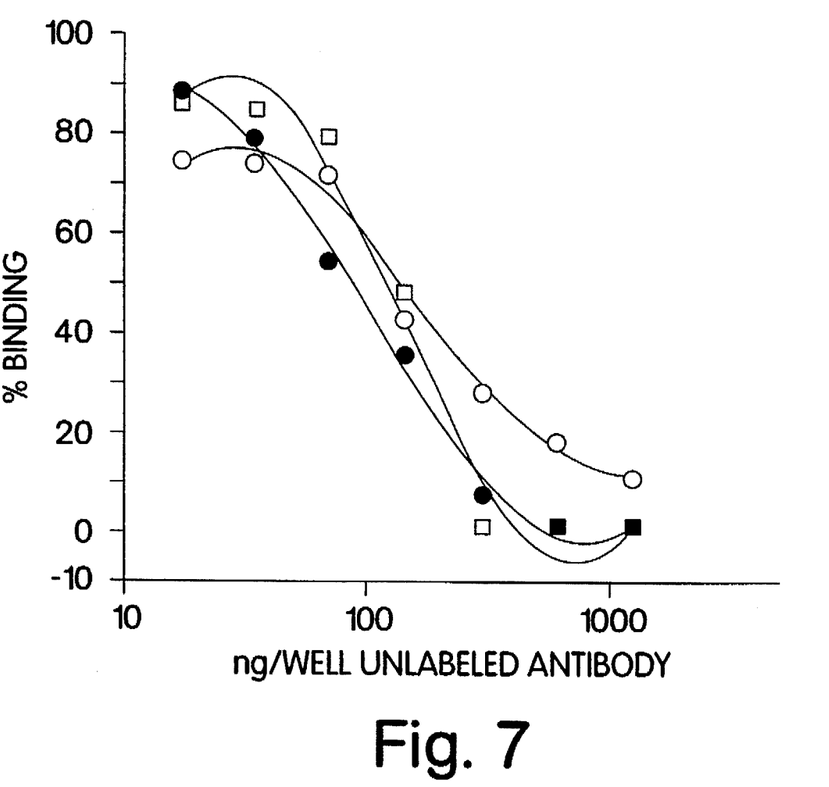
FIG. 7 is a graph of the antigen binding activity of Ig/LT immunoconjugates. Relative binding was determined in a competitive antigen binding assay using ch14.18 antibody conjugated to HRP as tracer and either unlabeled ch14.18 (o--o), CH2-LT (o--o, filled in) or labeled ch14.18 (¤--¤) as competitor.
Figure 8A:
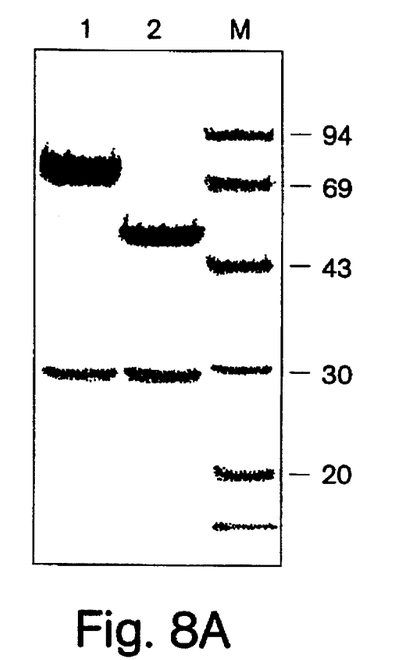
FIGS. 8A–B are strippled representations of an SDS-polyacrylamide gel showing an analysis, under reducing (R) or nonreducing (NR) conditions, of the fusion protein ch14.18-CH3-GM-CSF (lane 1) and the unfused protein ch14.18 (lane 2), where M is molecular weight markers of indicated sizes.
Figure 8B:
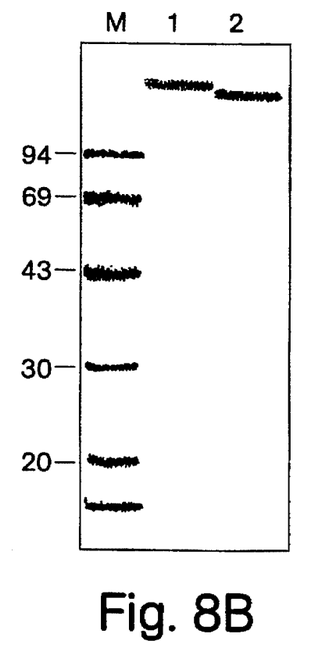
Figure 9:
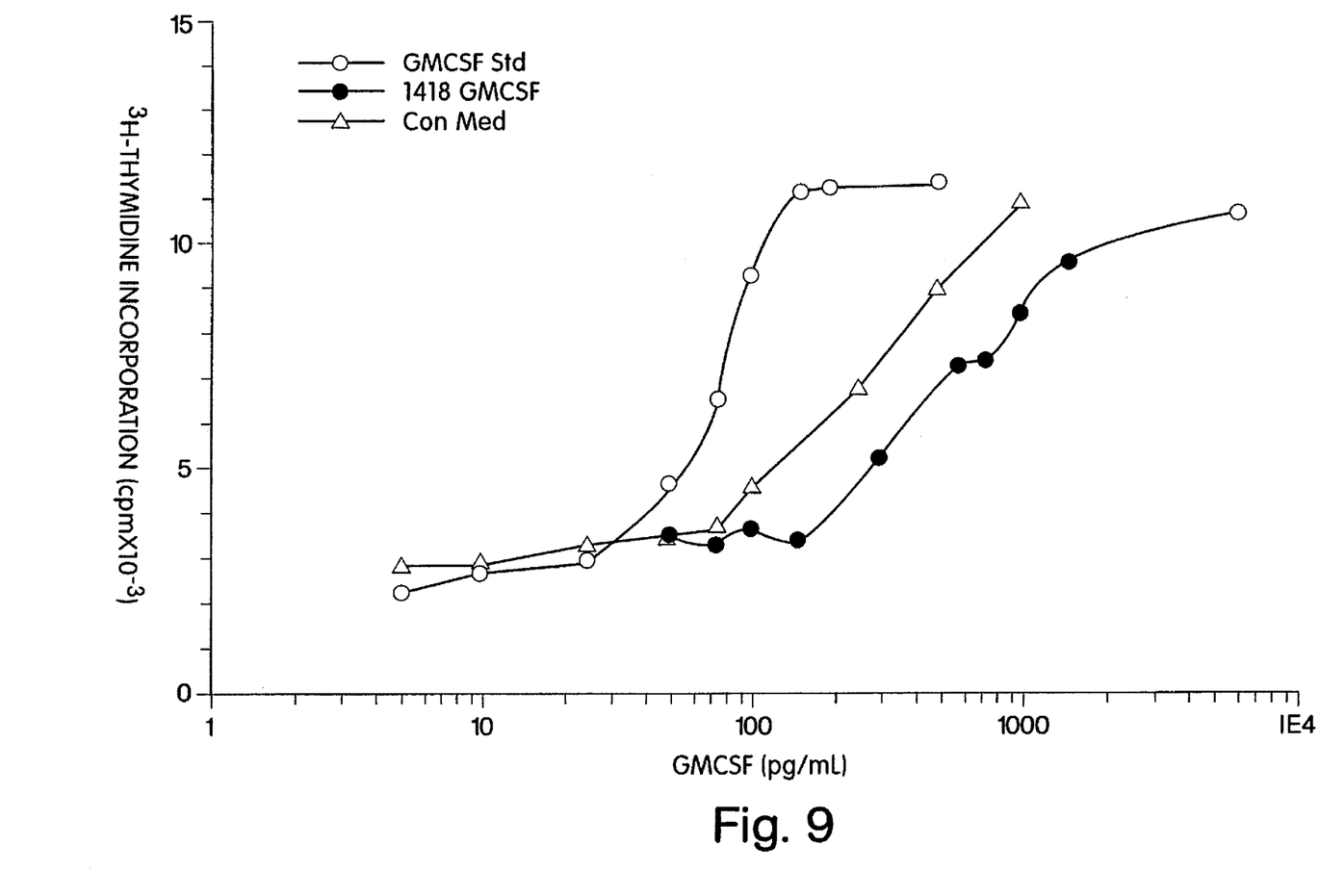
FIG. 9 is a graph of GM-CSF activity of the Ig/GM-CSF immunoconjugate ch14.18-GM-CSF (o--o, filled in) compared to a GM-CSF standard (o--o) and conditioned medium (Δ--Δ).

An alternative purification scheme was developed in which the pH was not reduced to below 6.5. The material from this preparation was compared to that purified by protein A, the original starting material, and the LT standard. The results of the LT cytostatic assay, in the absence of mitomycin C, shown in FIG. 5, demonstrate that full LT activity can be maintained during purification provided low pH is avoided. This assay was used to give a better dose response for the LT control and to demonstrate that the relationship between CH2-LT and CH3-LT is consistent for both assay systems. The same results were obtained in the cytolytic assay.

The results show that full activity (as measured by this assay) can be maintained when LT is fused to an Ig H chain. The fact that the LT amino terminus is covalently bound to the carboxy-terminus of the antibody apparently does not prevent LT receptor binding or the steps subsequent to binding that are required for activating the cell killing process.

7. Antigen Binding and Effector Functions of Ig/LT immunoconjugates

The antigen binding activity of the immunoconjugates was measured on antigen-coated plates in either a direct binding or competition assay format. In the direct binding assay antigen binding activity was found to be much higher than that of the control ch14.18 antibody. Since the source of the GD2 antigen was a crude membrane extract from neuroblastoma cells, it is possible that the TNF/LT receptor is present in the preparation and that binding of the conjugate through the LT domain is responsible for this increased activity. When antigen binding was measured in a competition assay, the conjugate was found to compete with the labeled ch14.18 antibody for antigen only slightly more efficiently than the unlabeled ch14.18 antibody (FIG. 7).

The results show that it is possible to combine the antigen binding activity of an anti-tumor cell antibody with the potent biological activity of a cytokine. The presence of the CH3 exon in the immunoconjugate results in complete H-chain assembly and, as a consequence, higher LT and effector activities. The assembly of H chains may likely result in LT dimerization.

In addition, a free amino terminus is not necessary for LT binding to its receptor since in the highly active CH3-LT immunoconjugate, the amino terminus of the LT domain is peptide bonded to the Ig H chain.

8. Construction and Expression of Ig/GM-CSF Immunoconjugates

Ig/GM-CSF conjugates were made by joining a nucleotide sequence encoding GM-CSF to a nucleotide sequence encoding an Ig heavy chain, such that the encoded protein includes a heavy chain fused via the carboxy terminus to GM-CSF. The construct was made as follows. The mature protein coding sequence of GM-CSF was linked to the end of the CH3 exon of the human $C\gamma_1$ gene using PdHDL2 and appropriate oligonucleotide linkers, as described above for the LT conjugate and according to procedures well-known in the art. Also as described above for LT conjugates, the Ig heavy chain GM-CSF fused gene was combined with the heavy chain V region gene of the 14.18 anti-GD2 heavy chain, and carried on the same vector as the human Cκ gene and the light chain V region gene of the 14.18 antibody. After transfection of the DNA into hybridoma cells and consequent expression of the H and L genes, a complete ch14.18 antibody with GM-CSF attached to the end of each H chain was produced. The fusion protein was purified from conditioned medium using adsorbtion to and elution from protein A Sepharose. The peak material was diafiltered using an Amicon stirred cell into PBS and concentrated to approximately 1 mg/mL.

The fusion protein was analyzed by electrophoresis on a 10% SDS-polyacrylamide gel (FIG. 8) under reducing (R) or non-reducing (NR) conditions and the proteins were visualized by staining with Coomassie Blue. Lane 1, ch14.18-CH3-GMCSF; Lane 2, ch14.18; M, molecular weight markers of the indicated sizes in kD. The relative molecular weight of the fused H chain of 75 kD in lane 1 (R) is consistent with a glycosylated GM-CSF (~25 kD) being fused to the H chain (50 kD). Note in the non-reduced lane 1 that the fusion protein is assembled into a single high molecular weight species of ~200 kD.

9. Biological Activity of Ig/GM-CSF Conjugates

The GM-CSF activity of the ch14.18-GM-CSF fusion protein was examined in a proliferation assay using the GM-CSF-dependent cell line AML-193 (human acute myelogenous leukemia) (obtained from Daniel Santoli, Wistar Institute, Philadelphia, Pa.). Cells are cultured for 2 days in serum-free medium containing insulin and transferrin (but no GM-CSF), at which time GM-CSF or fusion protein sample dilutions are added. After five more days, 5 μCi of $^{3}H$-thymidine is added to each well and after 16 hr, the cells are harvested in 10% trichloroacetic acid. After 30 min. on ice the precipitated material is collected on GF/C filters, dried and counted by liquid scintillation.

In FIG. 9, the proliferation obtained with varying amounts of GM-CSF, conditioned medium containing the secreted fusion protein, or ch14.18-GM-CSF purified by protein A Sepharose are compared. The results show that significant GM-CSF activity is maintained once the molecule is fused to the H-chain but that the activity is either 20% (conditioned medium) or 10% that of (purified fusion protein) GM-CSF standard. Maximum incorporation was obtained with less than 10 ng/mL of the purified fusion protein (GM-CSF equivalents or 50 ng of total protein). This slight loss of activity is not likely to affect the utility of this fusion protein, especially if large amounts of ch14.18-GM-CSF accumulate at the site of solid tumors expressing the GD2 antigen.

The in vivo half-life of the immunoconjugate was determined by injecting mice (20 μg injected in the tail vein) with ch14.18-GM-CSF. Samples of blood were collected at the indicated times and the amount of fusion protein in the serum was determined by ELISA. The capture antibody was a polyclonal goat anti-human IgG (Fc-specific) and the detecting antibody was a horseradish peroxidase-conjugated goat anti-human K. As seen in Table 1, the half-life (calculated between the 24 hr and 4 day time points) was nearly 3 days. This compares to the published value of 85 min. in humans (Herrmann et al. (1989) J. Clin Oncol. 7:159–167). This increased half-life may compensate for the reduced activity of the fusion protein, especially since the local concentration of the immunoconjugate at the tumor site is likely to be increased by antibody targeting.

TABLE 1

| Serum Concentration of ch14.18-CH3-GM-CS | |
|---|---|
| Time after injection | Ab Concentration (ng/mL |
| 4 hr | 9210 |
| 16 hr | 9660 |
| 24 hr | 5950 |
| 4 days | 2530 |

Mice were injected with 20 µg of the ch14.18-CH3-CSF fusion protein in the tail vein. Small samples (~50 µL) were taken from the tail vein and assayed for human antibody determinants.

10. Construction, Expression, and Activity of Ig/TNF Immunoconjugates

Ig/TNF immunoconjugates were made by fusing nucleotide sequences encoding TNFα and immunoglobulin heavy chain such that TNFα is fused to the carboxy terminus of the heavy chain. Briefly, the mature TNFα coding sequence was fused to the end of the human Cγ1 CH3 exon using oligonucleotides. The recombined fragment was joined downstream of the heavy chain V region encoding gene from the anti-GD2 mouse antibody 14.18; also contained in this vector was the human k gene, including both the V region gene encoding the light chain V region from the anti-GD2 mouse antibody 14.18 and the C region encoding gene. Hybridoma cells were transfected and selected as described above. Clones secreting human antibody determinants were expanded and used for the production and purification of the ch14.18-CH3-TNFα fusion protein by protein A Sepharose chromatography. The activity of the fusion protein was tested as described above for the CH3-LT fusion proteins.

Figure 10:
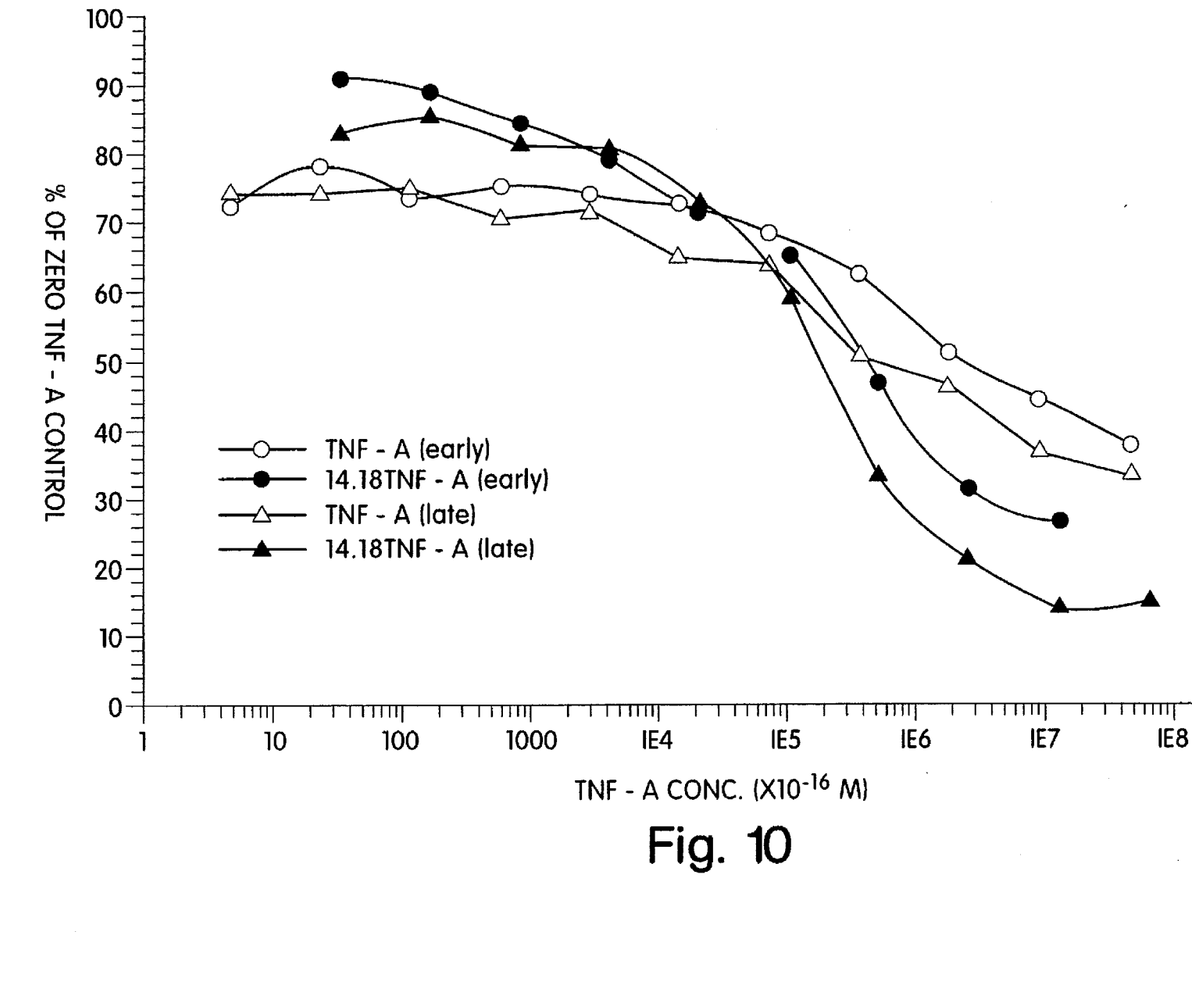
FIG. 10 is a graph of TNF-α activity of the Ig/TNF immunoconjugatees ch14.18-TNF-α (early) (o--o, filled in), ch14.18-TNF-α (late) (Δ--Δ, filled in), compared to TNF-α (early) (o--o) and TNF-α (late) (Δ--Δ).

As seen in FIG. 10, the amount of cytotoxicity obtained with the fusion protein met or exceeded that of native TNFα at either early (20 hr) or late (24 hr) points in the assay. This fusion protein appears to be fully functional with respect to TNFα activity, even though it was purified using protein A Sepharose. The CH3-LT construct was partially inactivated by the elution at acidic pH using the same protocol.

The results described above for the Ig/LT, Ig/GM-CSF, and Ig/TNFα immunoconjugates demonstrate that an antibody can be genetically fused to a cytokine without the loss of antigen binding activity and effector functions of the antibody, or the receptor binding and biological activity of a cytokine.

11. Dosage

Immunoconjugates of the invention may be administered at a therapeutically effective dosage within the range of lug-100 mg/kg body weight per day. The immunoconjugate may be administered in physiologic saline or any other biologically compatible buffered solution. This solution may be administered systemically (e.g., by injection intravenously or intramuscularly).

Other Embodiments

The invention may be embodied in other specific forms without departing from the spirit or essential characteristics thereof. The present embodiments are therefore considered to be in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A recombinant immunoglobulin (Ig) chain comprising:

an Ig heavy chain and a cytokine which elicits a cytokine-specific biological response by a cell bearing a receptor for said cytokine, said Ig heavy chain comprising an N-terminal variable region specific for a cell bearing a cell surface antigen; and, CH1 and CH2 domains, said Ig heavy chain being joined at its carboxy-terminus by a peptide bond to the amino terminal amino acid of the cytokine.

2. The recombinant Ig chain of claim 1, wherein the Ig heavy chain further comprises the CH3 domain.

3. The recombinant Ig chain of claim 1, wherein a proteolytic cleavage site is located between the Ig heavy chain and the cytokine.

4. The recombinant Ig chain of claim 1, wherein the variable region is a mouse Ig variable region and the CH1 and CH2 domains are human Ig CH1 and CH2 domains.

5. The recombinant Ig chain of claim 1, wherein the variable region of the Ig heavy chain is specific for a cell surface antigen of a cancer cell or a virus-infected cell.

6. The recombinant Ig chain of claim 5, wherein said cell surface antigen is a tumor associated antigen or a viral antigen.

7. The recombinant Ig chain of claim 1, wherein the cytokine is tumor necrosis factor alpha.

8. The recombinant Ig chain of claim 1, wherein the cytokine is interleukin-2.

9. The recombinant Ig chain of claim 1, wherein the cytokine is a lymphokine.

10. The recombinant Ig chain of claim 9, wherein the lymphokine is a lymphotoxin.

11. The recombinant Ig chain of claim 9, wherein the lymphokine is granulocyte-macrophage colony stimulating factor.

12. The recombinant Ig chain of claim 9, wherein the lymphokine is a lymphokine which forms a dimeric or multimeric structure.

13. A cytokine immunoconjugate comprising:

(a) a recombinant immunoglobulin (Ig) heavy chain having an N-terminal variable region specific for a cell bearing a cell surface antigen of a cancer cell or a virus-infected cell, a constant region comprising CH1 and CH2 domains, and a cytokine joined to the carboxy-terminus of said constant region by a peptide bond, wherein said cytokine elicits a cytokine-specific biological response by a cell bearing a receptor for said cytokine; and (b) an Ig light chain having a variable region specific for said cell surface antigen, said Ig heavy and light chains forming together a functional antigen-binding site, such that said immunoconjugate displays both antigen-binding specificity and cytokine biological activity.

14. The immunoconjugate of claim 13, wherein the recombinant Ig heavy chain has a constant region further comprising a CH3 domain.

15. The immunoconjugate of claim 13, wherein the cytokine is interleukin-2.

16. The immunoconjugate of claim 13, wherein the cytokine is tumor necrosis factor alpha.

17. The immunoconjugate of claim 13, wherein the cytokine is a lymphokine.

18. The immunoconjugate of claim 17, wherein the lymphokine is lymphotoxin.

19. The immunoconjugate of claim 17, wherein the lymphokine is granulocyte-macrophage stimulating factor.

20. The recombinant Ig heavy chain of claim 1 or 13 wherein said cytokine elicits a cytotoxic response by cells bearing a receptor for said cytokine.

21. The recombinant Ig heavy chain of claim 1 or 13 wherein said cytokine elicits a proliferative response by cells bearing a receptor for said cytokine.

* * * * *